(12) United States Patent
Ragatz et al.

(10) Patent No.: US 8,851,017 B2
(45) Date of Patent: Oct. 7, 2014

(54) CARRYING TRAY FOR MODULAR ANIMAL IMAGING APPARATUS

(75) Inventors: Andrew George Ragatz, Gretna, NE (US); Donald Thomas Lamb, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 412 days.

(21) Appl. No.: 13/163,584

(22) Filed: Jun. 17, 2011

(65) Prior Publication Data
US 2011/0239954 A1   Oct. 6, 2011

Related U.S. Application Data

(62) Division of application No. 11/850,556, filed on Sep. 5, 2007, now Pat. No. 8,220,415.

(51) Int. Cl.
*A01K 1/03*   (2006.01)
*A61B 5/00*   (2006.01)

(52) U.S. Cl.
CPC ........... *A61B 5/0059* (2013.01); *A61B 2503/40* (2013.01)
USPC .......................................... 119/420; 119/417

(58) Field of Classification Search
USPC .................. 119/417–420, 28.5, 753, 755, 756
See application file for complete search history.

(56) References Cited

U.S. PATENT DOCUMENTS 4,610,490 A   9/1986   Naito et al.
4,721,060 A * 1/1988   Cannon et al. ................. 119/420

(Continued)

FOREIGN PATENT DOCUMENTS

CN   1896664 A   1/2007
EP   1568986 A1  8/2005

(Continued)

OTHER PUBLICATIONS

International Search Report and Written Opinion mailed on Nov. 14, 2008, for International Application No. PCT/US2008/075103.

(Continued)

*Primary Examiner* — Kimberly Berona
(74) *Attorney, Agent, or Firm* — Leydig, Voit & Mayer; Gerald T. Gray

(57) ABSTRACT

An imaging system that allows for unhindered access to a sample to be imaged. A housing structure is configured with a drawer having a platform. The platform may be configured to hold a sample, such as an animal, and/or the platform may be configured to mate with a sample holding member, such as a removable carrying tray for holding the sample. The drawer presents the platform to an imaging device or system internal to the housing when in a closed, or imaging, state. When in an extended state, the drawer presents the platform external to the housing to allow unobstructed manipulation of a sample on the drawer platform (or on the sample holding member on the platform). When used, a sample holding member such as a removable carrying tray may be docked with the drawer platform, and various interconnects, such as gas ports and electrical connectors, on the sample holding member engage with corresponding elements on the platform when docked. The tray may be undocked and moved to a remote location having a compatible docking station to allow for preparation or processing of a sample elsewhere. The tray may be docked with a docking station located at a sample preparation station. In the case of a live animal sample, the preparation station may include a sterile hood or other laboratory location.

15 Claims, 13 Drawing Sheets

(56) References Cited

U.S. PATENT DOCUMENTS

| | | | |
|---|---|---|---|
| 5,320,069 A * | 6/1994 | Anderson et al. | 119/751 |
| 5,802,991 A | 9/1998 | Brown et al. | |
| 6,008,892 A | 12/1999 | Kain et al. | |
| 6,357,394 B1 | 3/2002 | Waters et al. | |
| 6,458,410 B1 | 10/2002 | Ikami et al. | |
| 7,086,350 B2 | 8/2006 | Tecott et al. | |
| 7,140,703 B1 | 11/2006 | Holdgate, III | |
| 7,464,707 B2 | 12/2008 | Dalgetty et al. | |
| 7,466,418 B2 | 12/2008 | Nilson et al. | |
| 7,474,398 B2 | 1/2009 | Nilson et al. | |
| 7,474,399 B2 | 1/2009 | Nilson et al. | |
| 7,529,338 B2 | 5/2009 | Fung et al. | |
| 7,595,838 B2 | 9/2009 | Nilson et al. | |
| 7,636,966 B2 * | 12/2009 | Gallant et al. | 5/600 |
| 7,663,664 B2 | 2/2010 | Rice et al. | |
| 7,765,487 B2 | 7/2010 | Cable | |
| 7,784,429 B2 | 8/2010 | Chiodo | |
| 7,911,485 B2 | 3/2011 | Rykowski et al. | |
| 8,028,663 B2 * | 10/2011 | Chen et al. | 119/729 |
| 8,342,136 B2 * | 1/2013 | Hadjioannou et al. | 119/755 |
| 2003/0154976 A1 | 8/2003 | Dalgetty et al. | |
| 2003/0164703 A1 * | 9/2003 | Ferris et al. | 324/318 |
| 2005/0148846 A1 | 7/2005 | Cable et al. | |
| 2005/0219358 A1 | 10/2005 | Cable et al. | |
| 2005/0231592 A1 | 10/2005 | Cable et al. | |
| 2006/0203243 A1 | 9/2006 | Nilson et al. | |
| 2006/0203244 A1 | 9/2006 | Nilson et al. | |
| 2006/0283460 A1 | 12/2006 | Brown et al. | |
| 2007/0089685 A1 | 4/2007 | Gottlieb et al. | |
| 2007/0127118 A1 | 6/2007 | Nilson et al. | |
| 2008/0079802 A1 | 4/2008 | Nilson et al. | |
| 2008/0099020 A1 | 5/2008 | Nelson | |
| 2008/0150662 A1 * | 6/2008 | Broumand | 335/285 |
| 2009/0141862 A1 | 6/2009 | Dunham et al. | |
| 2010/0056899 A1 * | 3/2010 | Toddes et al. | 600/411 |
| 2010/0101500 A1 * | 4/2010 | Sannie et al. | 119/420 |
| 2011/0079734 A1 | 4/2011 | Grodzins et al. | |
| 2012/0226288 A1 * | 9/2012 | Mays et al. | 606/116 |
| 2012/0278990 A1 * | 11/2012 | Lanz et al. | 5/601 |
| 2012/0330130 A1 * | 12/2012 | Lanz et al. | 600/411 |

FOREIGN PATENT DOCUMENTS

| | | | | |
|---|---|---|---|---|
| JP | 02249536 A | | 10/1990 | |
| JP | 2001321015 A | * | 11/2001 | A01K 67/00 |
| JP | 2009192425 A | | 8/2009 | |
| RU | 2048757 | * | 11/1995 | |
| WO | WO 98/30886 A1 | | 7/1998 | |
| WO | WO 2009/120758 A1 | | 10/2009 | |
| WO | WO 2010/080016 | | 7/2010 | |

OTHER PUBLICATIONS

European Search Report for European Patent Application No. 08799109.7 issued Nov. 28, 2013.

* cited by examiner

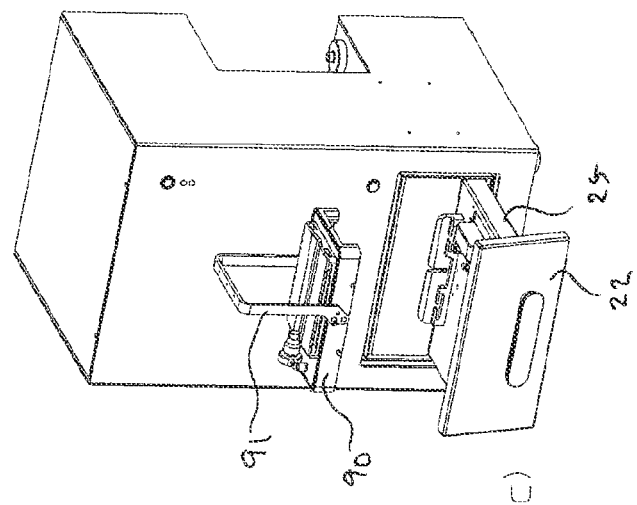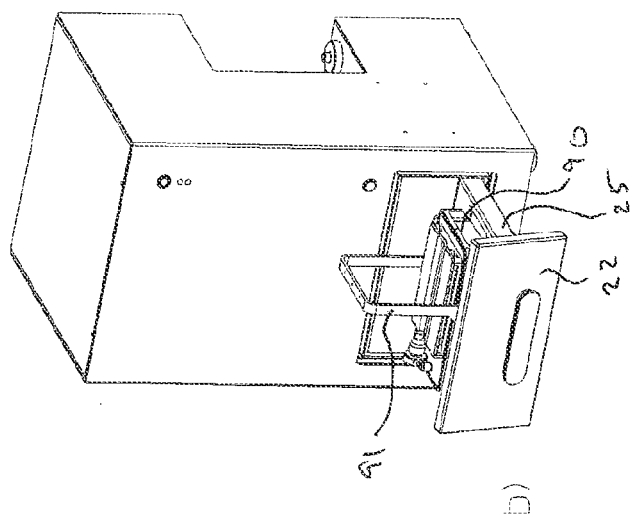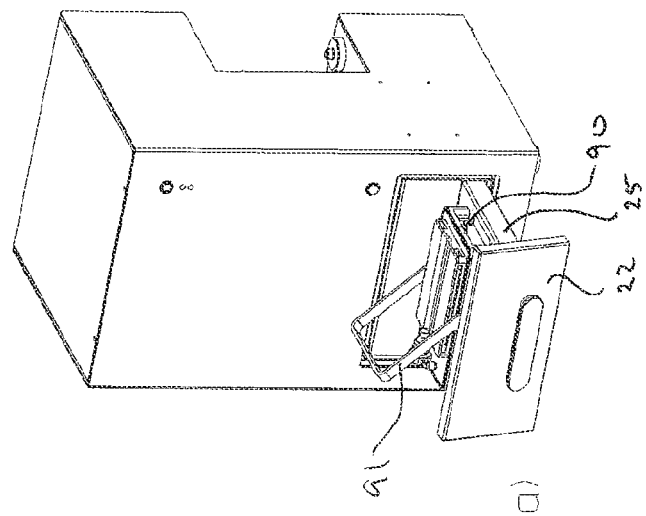
FIG. 7

FIG. 10
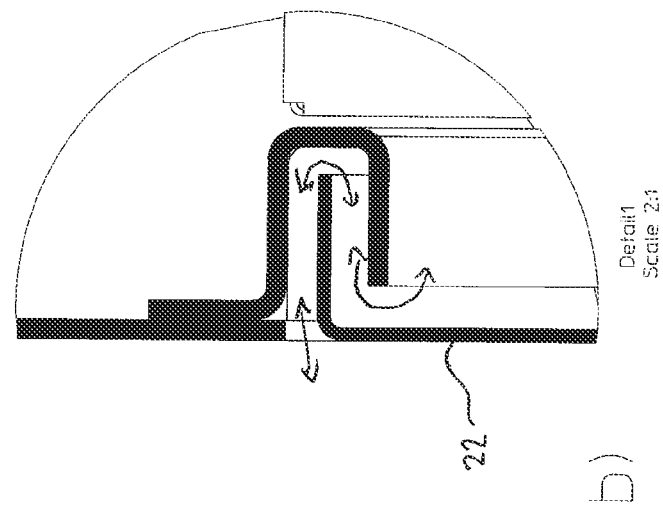
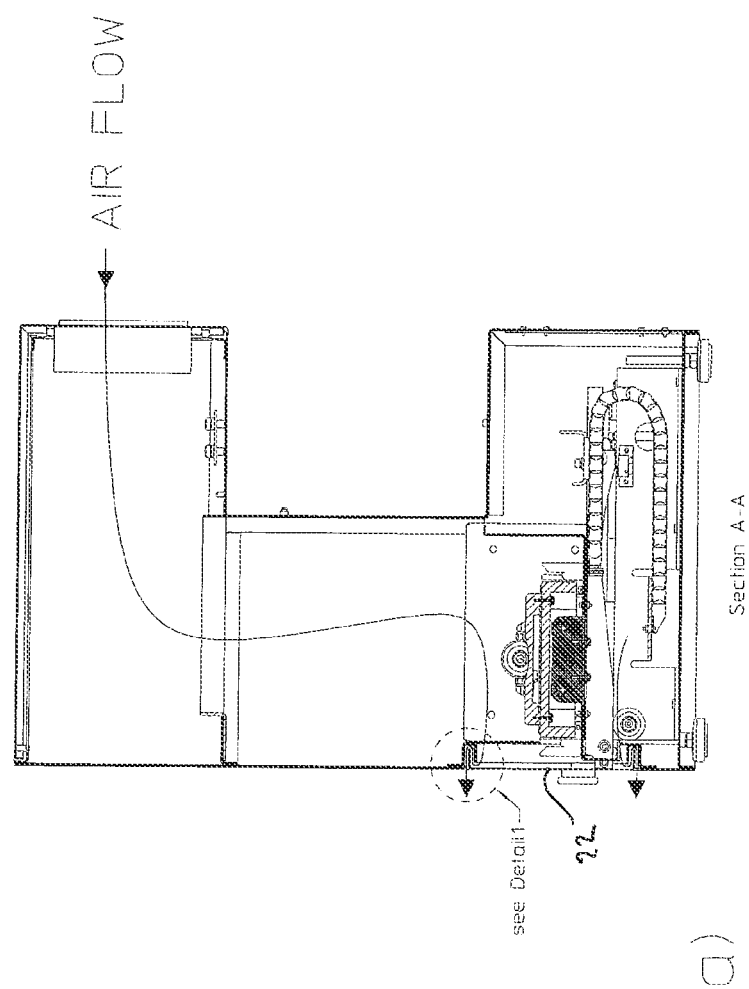

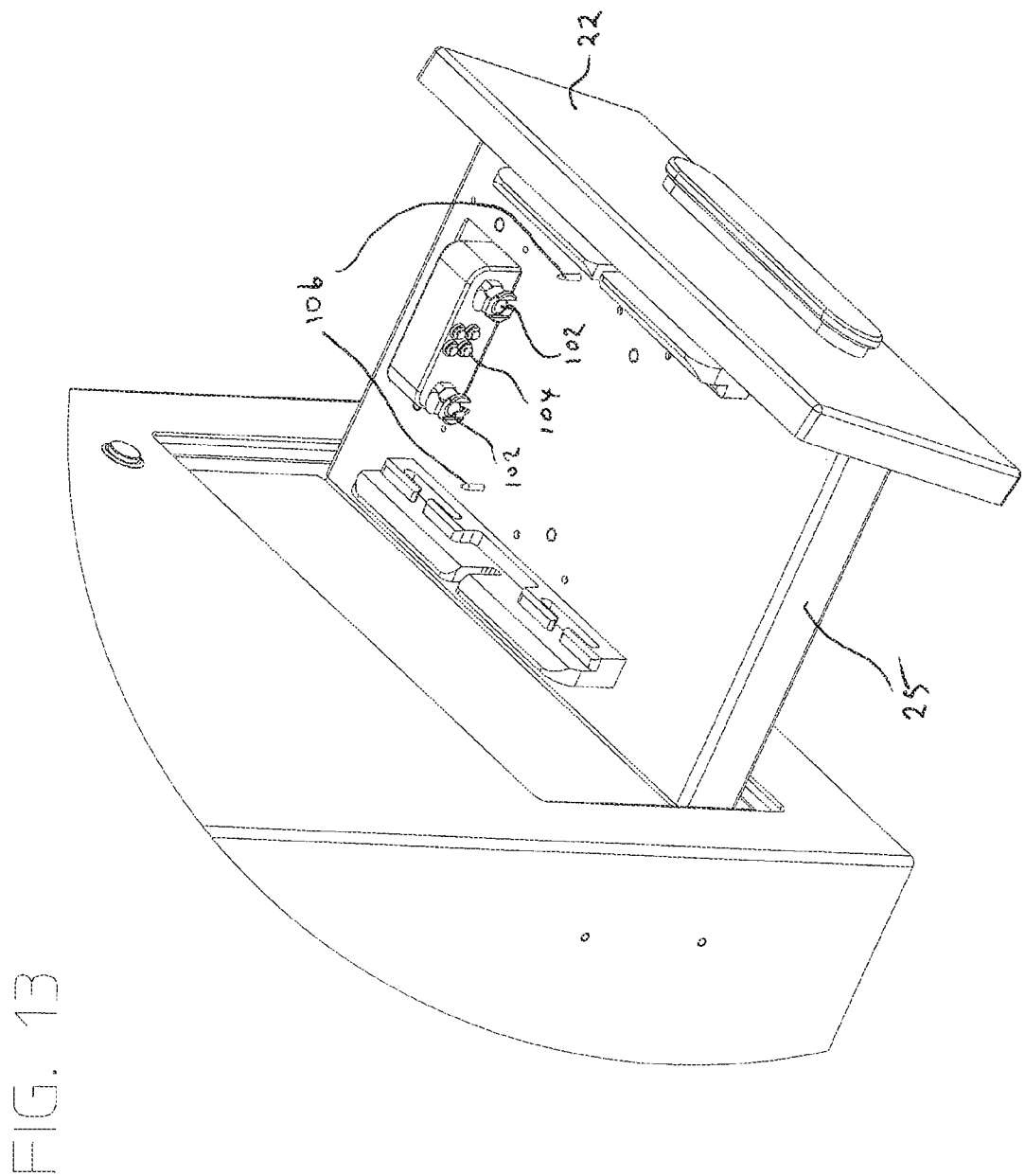

CARRYING TRAY FOR MODULAR ANIMAL IMAGING APPARATUS

CROSS-REFERENCES TO RELATED APPLICATIONS

This application is a divisional of U.S. patent application Ser. No. 11/850,556, filed Sep. 5, 2007 entitled MODULAR ANIMAL IMAGING APPARATUS AND METHOD OF USE which is hereby incorporated by reference, along with all other references cited in this application.

BACKGROUND

The present invention relates generally to imaging systems, and more particularly to animal imaging systems and methods that facilitate user interaction with samples such as live animals.

Current imaging systems for imaging animal specimens typically provide an imaging apparatus in an enclosed volume. The enclosed volume is desirable for keeping unwanted or stray light from adversely affecting the images of a sample under investigation. The source or location of detected light from within the sample helps identify portions of the sample, such as traced molecules in a particular portion of a mouse, where an activity of interest may be taking place. Certain in-vivo imaging applications, for example, might include analysis of detected fluorescent or luminescent emissions from internal or external portions of the sample. Analysis of these emissions enable one to better understand characteristics of the activities or interactions taking place on or within the sample.

Detecting the lumninescent or fluorescent emissions may involve image capture over a short period of time or over an extended period of time, e.g., seconds or minutes. A live sample is typically anesthetized during this time period to prevent movement that could compromise the image capture process. Additionally, time series images of the sample may be taken in certain analyses.

Current animal image detection systems typically include an enclosed box with an internal imaging system. An opening is typically provided to allow access to the interior. The sample generally needs to be positioned within the box at an appropriate position, and orientation, to enable effective imaging. However, manipulation of the sample within a constrained volume of the box can be tedious and problematic; access to the interior of a small instrument adversely limits the user interaction. For example, user manipulation and adjustment of sample restraints and/or a nosecone can be particularly difficult in the constrained volume provided by current systems. Further, for certain samples, such as mice having immune deficiencies, it may be necessary or desirable to control the environment for the sample as much as possible to reduce or prevent contamination of the sample. For example, transport of the sample between a hooded preparation station and the imaging device can present contamination issues that are inadequately addressed by current animal imaging systems.

Therefore it is desirable to provide animal imaging systems and methods that overcome the above and other problems.

BRIEF SUMMARY

The present invention provides imaging systems and methods that facilitate user interaction with a sample. In particular, animal imaging systems and methods are provided that facilitate user interaction with the sample (e.g., sample preparation and manipulation) and with internal components of an imaging apparatus.

According to certain embodiments, an imaging system is provided that allows for unhindered access to a sample to be imaged. In certain aspects, a housing structure of an imaging system is configured with a drawer having a platform. In one aspect, the platform is configured to hold a sample, such as a live animal or a deceased animal. In another aspect, the platform is configured to mate with a sample holding member, such as a removable carrying tray for holding the sample. The drawer presents the platform to an imaging device or system internal to the housing when in a closed, or imaging, state. When in an extended state, the drawer presents the platform external to the housing to allow unobstructed manipulation of a sample on the drawer platform (or on the sample holding member on the platform). When used, a sample holding member such as a removable carrying tray may be docked with the drawer platform, and various interconnects, such as gas ports and electrical connectors, on the sample holding member engage with corresponding elements on the platform when docked. The tray may be undocked and moved to a remote location having a compatible docking station to allow for preparation or processing of the sample elsewhere. For example, in one aspect, the tray may be docked with a docking station located at a sample preparation station. In the case of a live animal sample, for example, the preparation station may include a sterile hood (e.g., a vented hood or a laminar or vertical flow hood) or other laboratory location. Different preparation stations with docking stations may have different capabilities.

According to one aspect of the present invention, an imaging apparatus is provided for analyzing an animal subject. The apparatus typically includes a housing having walls defining an interior, and an opening for receiving a drawer, and the drawer presents at least one animal subject to be imaged. In certain aspects, the drawer includes a platform adapted to mate with a carrying tray or platform that holds the animal subject to be imaged.

According to another aspect of the present invention, a drawer apparatus is provided for presenting an animal subject to be imaged. The drawer typically includes a platform that presents the animal subject, and a moveable door configured to cover an opening of an imaging system housing structure and provide a substantially light-tight seal when the drawer is in a recessed position within the housing structure. In certain aspects, the drawer includes a cam mechanism adapted to reposition the door away from the platform when in an extended position so as to provided unhindered access to the platform.

According to yet another aspect of the present invention, an imaging apparatus for analyzing a sample is provided. The apparatus typically includes a housing having walls defining an interior, and an opening for receiving a drawer. The apparatus also typically includes a drawer that includes a platform that presents a surface for receiving a sample or a sample holding member; wherein the drawer is slidably mounted to the housing proximal the opening so that the drawer when in an extended position presents the platform external to said housing, and when in a recessed position presents the platform to an imaging system in the interior of the housing. The apparatus also typically includes a moveable door configured to cover the opening when the drawer is in the recessed position. In certain aspects, the door provides a substantially light-tight seal when the drawer is in the recessed position. In certain aspects, the platform includes one or more of a gas port for providing gas to or from a remote location, and/or an electrical connector for providing power and/or control signals from a remote power and/or control source to and from one or more monitoring systems associated with the platform for monitoring physiological conditions of the sample. In other aspects, then platform and tray include one or more corresponding (additional or alternate) connection ports for transferring other fluids therebetween. In certain aspects, such fluids include cooling or heating fluids, intravenous fluids for living animals, waste or exhaust fluids and/or other fluids. In certain aspects, the remote location includes one of a gas source, a filter or a reservoir.

According to yet another aspect of the present invention, a carrying tray is provided for holding and transporting a living animal. The tray typically includes a platform that presents a surface for receiving and supporting a live animal, a nosecone mounted to the platform, the nosecone adapted to receive the nose of a live animal supported on the platform, one or more gas ports on an underside of the platform for coupling with an external source of gas and/or for exhausting gas, and one or more electrical connectors on an underside of the platform for coupling with external power and/or signal sources. The tray also typically includes a connection mechanism adapted to removably engage with a tray receiving member of an animal imaging system or a sterile workstation such that when engaged the one or more gas ports and the one or more electrical connectors mate with corresponding elements on the tray receiving member. In certain aspects, the platform includes one or more valves associated with the one or more gas ports, wherein each valve is opened or actuated (e.g., allows gas or other fluid to pass through the valve) when the tray engages the platform. Similarly, each valve is closed or deactivated when the tray disengages from the platform.

According to still another aspect of the present invention, a nosecone mount is provided for mounting a nosecone to a platform. The mount typically includes a ball joint having a conduit for providing gas to a mounted nosecone from a gas source, wherein when coupled with a nosecone, the ball joint enables rotational movement of the nosecone about a ball joint axis. The mount also typically includes a pair of elbow fittings coupled to the ball joint and configured to couple with a platform, the elbow fittings enabling rotation of the ball joint about an axis defined by the elbow fittings. In certain aspects, the ball joint axis is substantially perpendicular to the axis defined by the elbow fittings.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIGS. 1*a* and 1*b* illustrate a front perspective view with a sample platform drawer in an open state and a closed state, respectively; and FIG. 1*c* illustrates a rear perspective view.

FIG. 6*a* shows the sample platform drawer in a closed state; FIG. 6*b* shows the sample platform drawer opening and extending; FIG. 6*c* shows the sample platform drawer in an extended state with the door dropped down; and FIG. 6*d* shows a side view of the sample platform drawer in an extended state with the door dropped down.

FIG. 7 illustrates perspective views of the animal imaging system of FIG. 1 including a removable sample carrying tray: FIG. 7*a* shows the sample tray with a handle moving between a locked and an unlocked state; FIG. 7*b* shows the sample tray with the handle in an unlocked state; FIG. 7*c* shows the sample tray removed from the sample platform drawer.

FIG. 8*a* shows the sample tray with a handle pushed down (e.g., in a locked state when mated with a tray receiving mechanism) to allow unimpeded access to the sample platform; FIG. 8*b* shows a removable lid according to one embodiment; FIG. 8*c* illustrates a tray with the removable lid mounted thereon according to one embodiment.

FIG. 9*a* shows the door in a closed state; FIG. 9*b* shows the door lowering as the drawer extends; FIG. 9*c* shows the door in a lowered state when the drawer is in an extended state.

FIG. 10*a* illustrates a side view of an animal imaging system including a door in a closed state, including a light-blocking vent seal according to one embodiment; FIG. 10*b* shows a close-up of a light-blocking vent seal according to one embodiment.

FIG. 13 illustrates a close-up view of a sample drawer platform configured with ports and connectors adapted to mate with the ports and connectors of the carrying tray shown in FIG. 12.

DETAILED DESCRIPTION

According to various embodiments, an imaging system includes a housing structure configured with a drawer having a platform. In one aspect, the platform is configured to hold a sample, such as a live animal. In another aspect, the platform is configured to mate with a sample holding member, such as a removable carrying tray for holding the sample. The drawer, in one embodiment, presents the platform to an imaging device or system internal to the housing when in a closed, or imaging, state. When in an extended state, the drawer presents the platform external to the housing to allow unobstructed manipulation of a sample on the drawer platform (or on the sample holding member on the platform). When used, a sample holding member such as a removable carrying tray may be docked with the drawer platform. In certain aspects, various interconnects, such as gas ports and electrical connectors, on the sample holding member engage with corresponding elements on the platform when docked. The tray may be undocked and moved to a remote location to allow for preparation or processing of the sample elsewhere. For example, in one aspect, the tray may be docked with a docking station located at a sample preparation station. In the case of a live animal sample, for example, the preparation station may include a laminar flow hood to provide filtered air, or other hood or laboratory location. Different preparation stations with docking stations may have different capabilities.

The remaining description will discuss details of the imaging systems and methods with respect to samples including live animals. However, it should be appreciated that the various embodiments are suitable for use with other samples such as slides, microtiter plates, etc.

Figure 1:
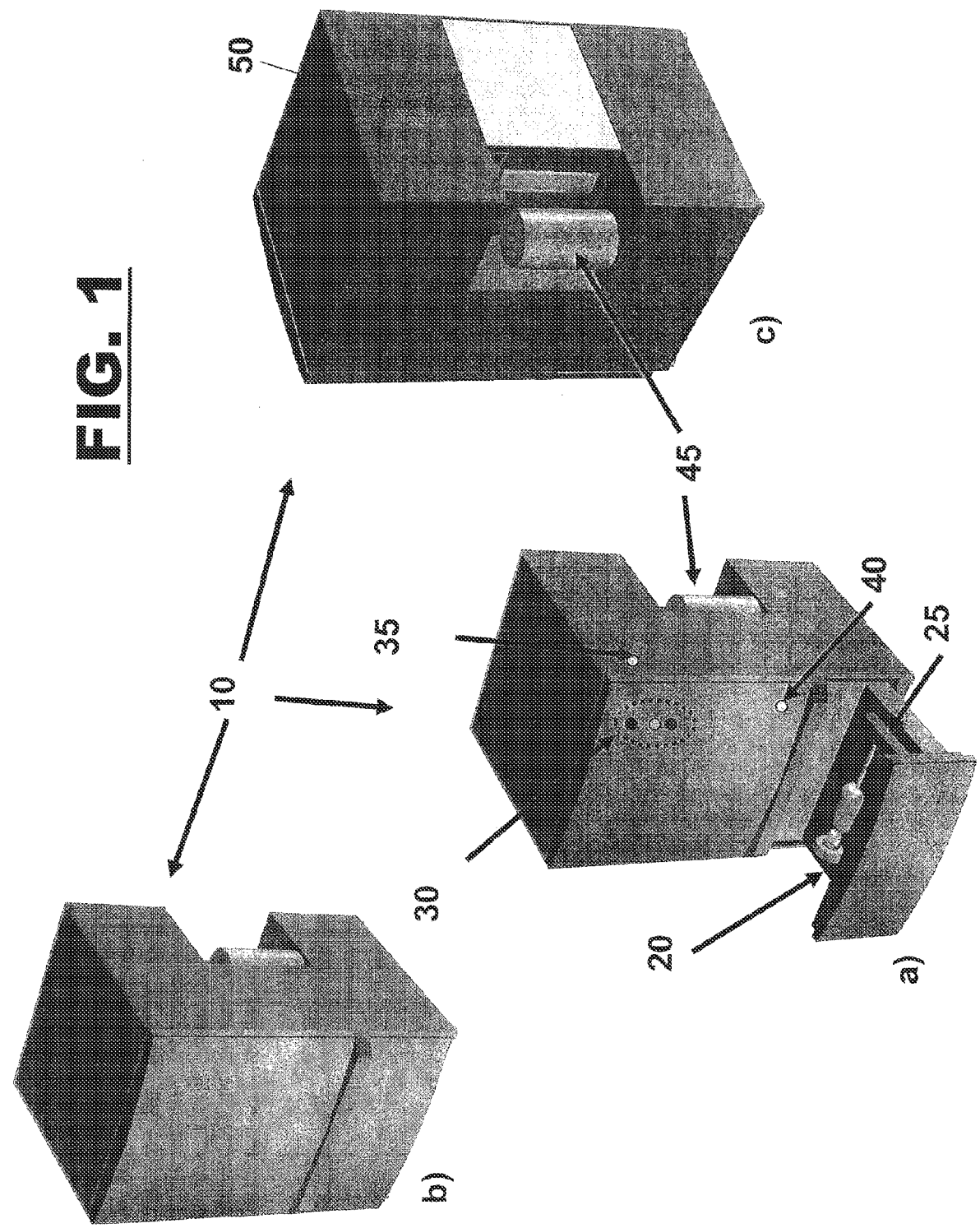
FIG. 1 illustrates perspective views of an animal imaging system according to one embodiment.

FIG. 1 illustrates an animal imaging system 10 according to one embodiment. As shown, system 10 includes a housing structure having walls defining an interior (not shown) and an exterior. An opening in a wall defines a pathway for receiving a sample platform drawer 20. The sample drawer 20 includes a platform 25 that presents a surface for receiving a sample. When in an extended state, a user may manipulate the sample on platform 25, unhindered by the interior components of system 10. When recessed into a closed state, the platform provides a sample thereon to an (internal) imaging system for imaging as will be discussed in more detail later. FIG. 1a shows system 10 with a sample platform drawer 20 in an open state and FIG. 1b shows the sample drawer 20 in a closed, or imaging, state. FIG. 1c shows a rear perspective view of system 10, including various external interface components 45. Useful interface components include connectors to power systems and/or computer systems, anesthesia or other gas or fluid sources, etc. A vent 50 is provided in one aspect to facilitate venting and/or air flow to or from internal portions of system 10.

As shown in FIG. 1a, in certain aspects, the housing structure of system 10 might include various status lights 30 to indicate operational states of system 10. Examples might include static and/or flashing LEDs for indicating an off state, an imaging state, a connected state, an error condition, etc. A power button 35 may also be provided to allow a user to activate the overall system power, and a drawer open and close button 40 may be provided to allow a user to activate or unlock the drawer 20. For example, in certain aspects, for a manually operated drawer, a user may depress a button to unlatch or unlock the drawer and/or a door coupled with the drawer to allow for manual movement of the drawer in and out of the housing structure. In other aspects, for an automated drawer, a button depress activates a motorized mechanism to open and close the drawer, e.g., automatically extend or retract the drawer. The drawer may be activated by other mechanical or electrical mechanisms as would be apparent to one skilled in the art.

Figure 2:
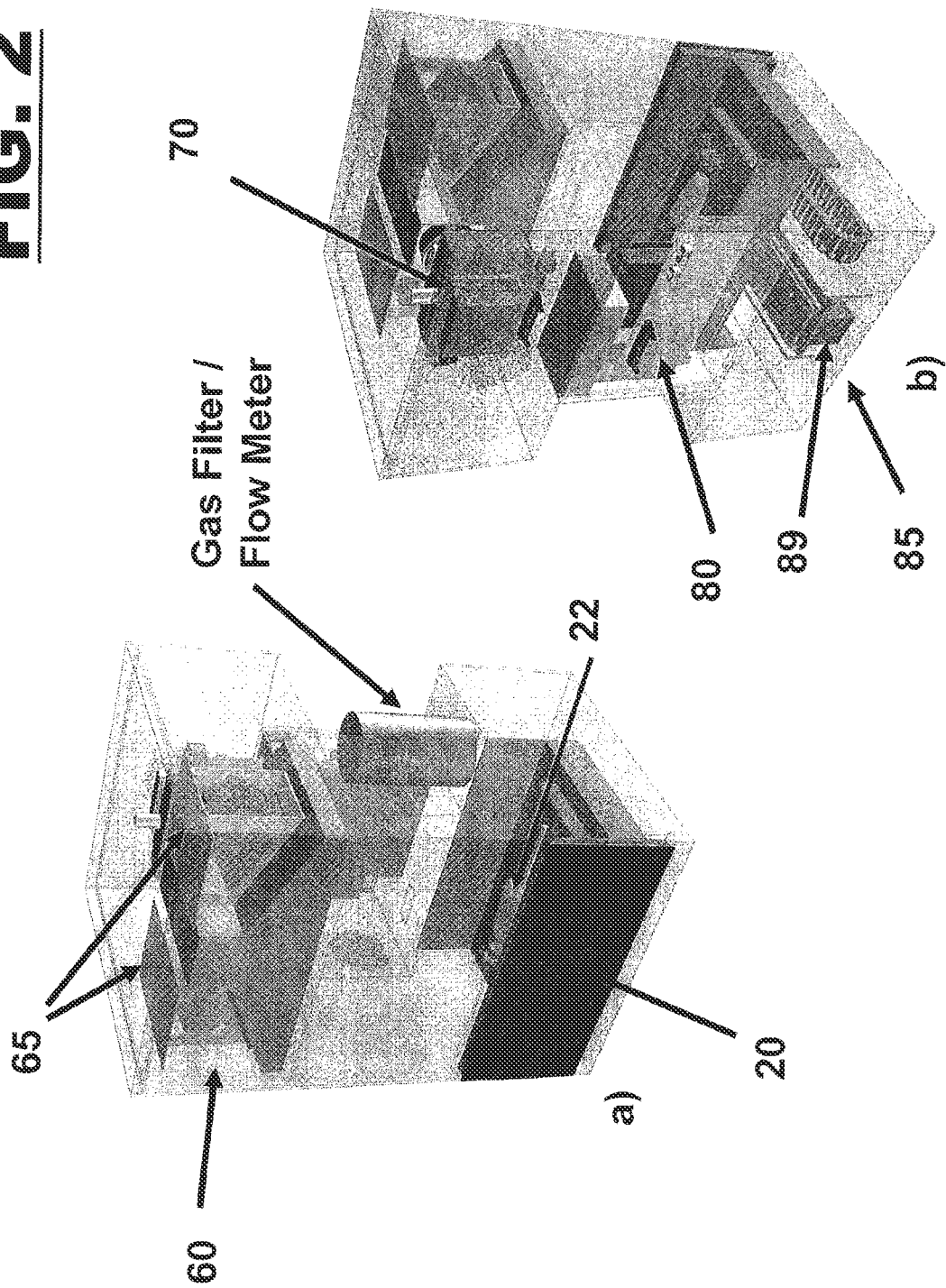
FIGS. 2*a* and 2*b* illustrates front perspective views of the animal imaging system of FIG. 1, including various internal components.

FIGS. 2a and 2b illustrate various internal components of animal imaging system 10 according to one embodiment: FIG. 2a shows a front perspective view and FIG. 2b shows a rear perspective view. As shown, system 10 in one embodiment includes an imaging system 60. In certain aspects, imaging system 60 includes one or more light sources 65 such as one or more laser modules, as well as an imaging device 70 such as a camera, CCD, APD or other light detection device(s) or component(s). Imaging system 60, in certain aspects, includes one or more filters, e.g., a filter wheel, to facilitate filtering the light presented to the imaging device, e.g., to remove undesired wavelengths. In fluorescence detection systems, for example, a filter is useful for removing stray (e.g., reflected) excitation light and/or to allow only light of a specific wavelength range to pass. As shown in FIG. 2, when in a closed state, a sample 22 on the platform 25 of drawer 20 is presented to the imaging system 60 in an interior of the housing structure to allow for illumination and/or excitation by light source(s) 65 and imaging by imaging device 70. In the case of fluorescence detection, for example, fluorescent moieties on or in the sample may be excited with one or more laser sources, and the sample may be imaged by the imaging device over a period of time, e.g., seconds or minutes, to determine characteristics of the sample. In the case of a live animal sample, for example, ingested fluorescent moieties may be analyzed to determine various physiological characteristics of the animal.

In certain aspects, system 10 includes an on-board control system 80 to control operation of various internal components, to store data, and/or to interface with external systems such as remote computer systems. For example, control system 80 in certain aspects includes one or more connectors to external system components such as network connection(s) to remote components or computer systems. More detail of control system 80 will be provided below with reference to FIG. 5.

Figure 3:
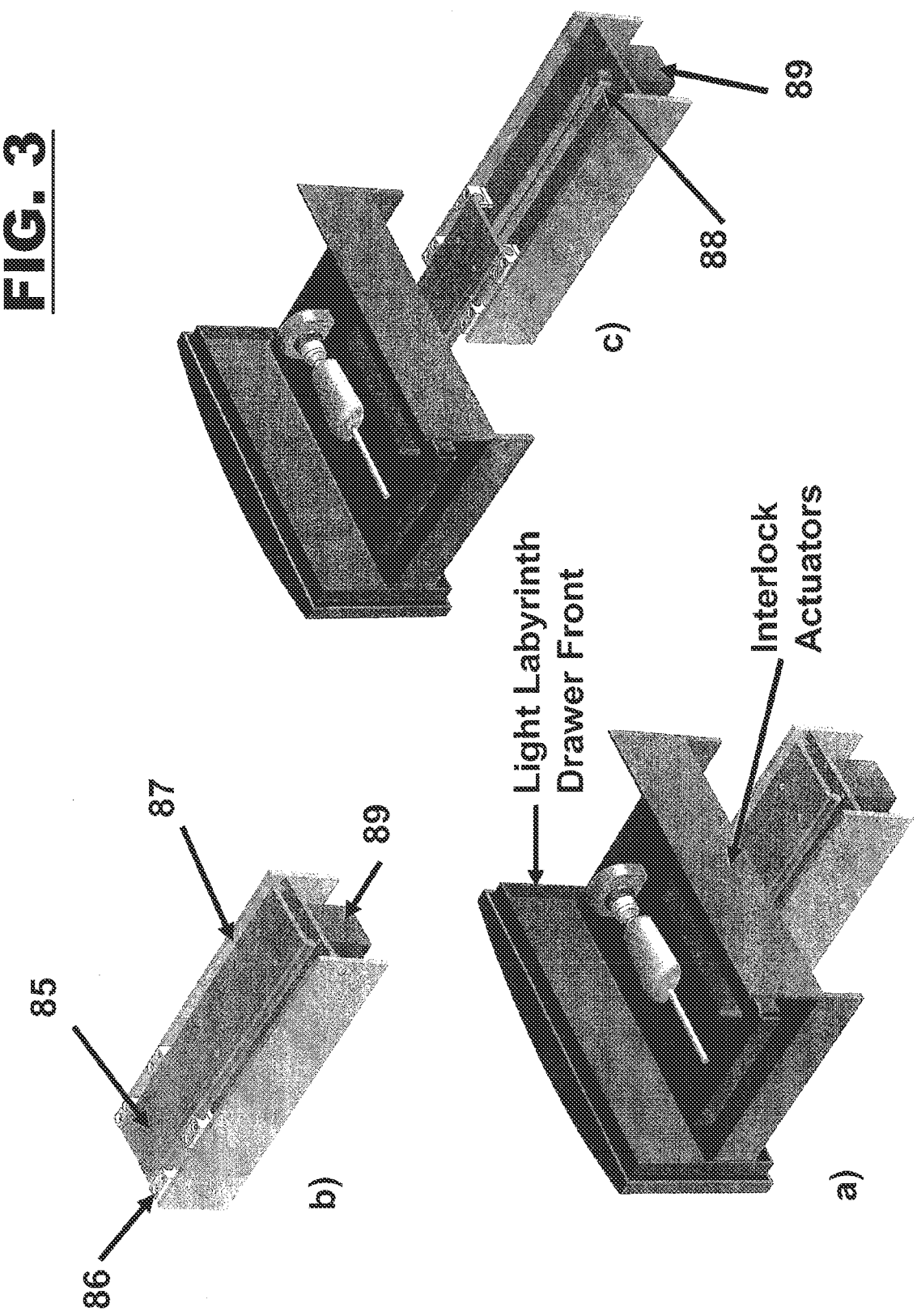
FIG. 3 illustrates various views of a sample platform drawer and drawer components according to one embodiment.

As shown in FIG. 2, a motor and bearing assembly 85 is provided in one aspect to facilitate automatic control of the drawer 20. FIG. 3 illustrates components of a motor and bearing assembly 85, according to one embodiment. A stationary bearing assembly 85 mounted internal to the structure of the imaging apparatus housing includes one or more bearings 86 that couple with drawer 20 and slide along assembly 85. A motor 89 (e.g., stepper motor) coupled with a drive belt 88 coupled to drawer 20 as shown in FIG. 3c according to one embodiment enables drawer 20 to be controlled to slide external to the housing and to retract. FIG. 3a shows the drawer 20 in a closed or retracted position on bearing assembly 85 and FIG. 3c shows the drawer 20 in an open position on bearing assembly 85. One or more switches 87 may be provided on bearing assembly 85 to detect positioning of the drawer 20 on bearing assembly 85 and to provide feedback to control system 80.

Figure 4:
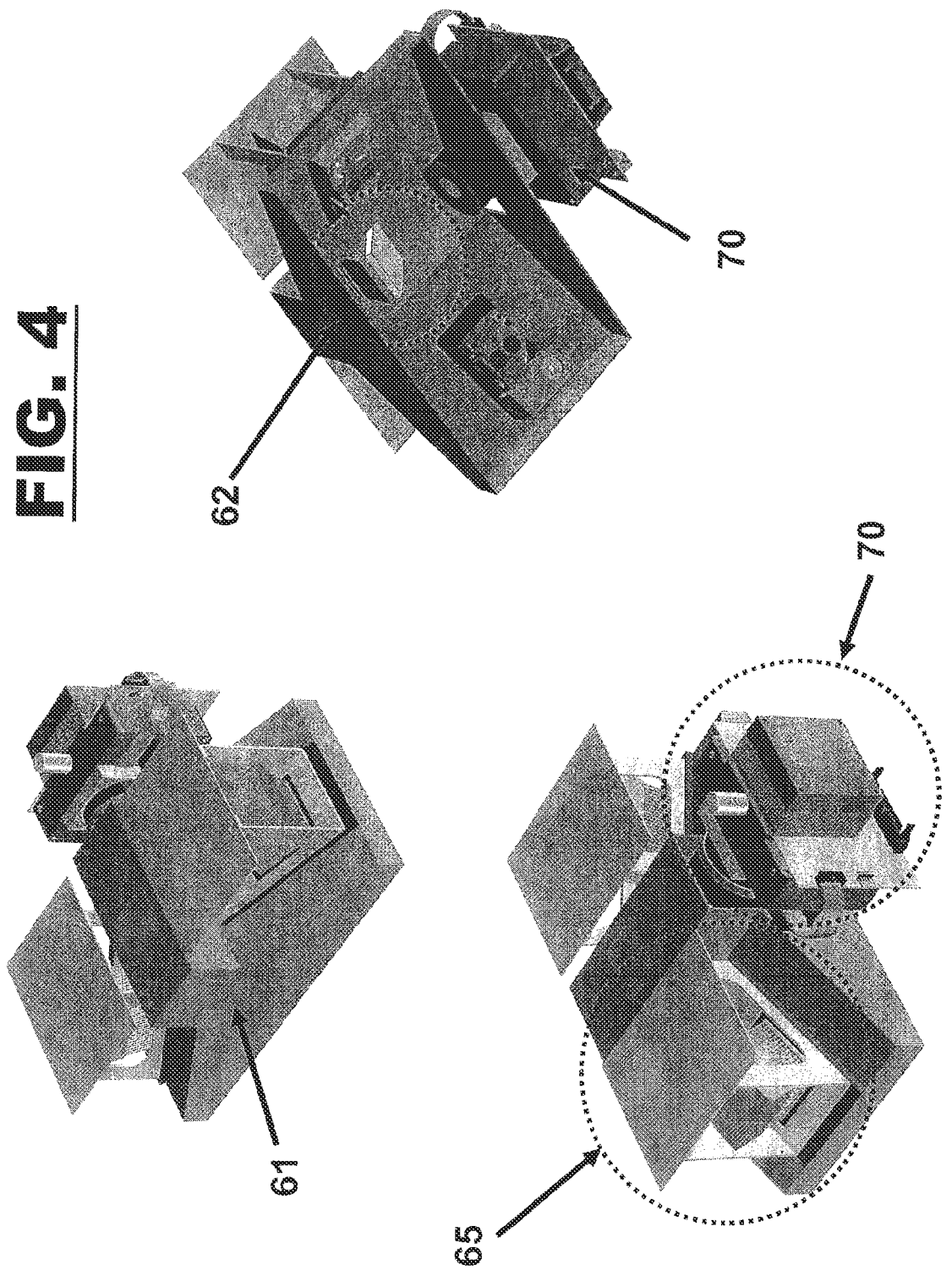
FIG. 4 illustrates various views of an imaging and excitation module according to one embodiment.

FIG. 4 illustrates various views of imaging system 60 according to one embodiment. Imaging system 60, in certain aspects, includes a mounting structure 61 for mounting components within the housing structure of system 10. In one aspect, one or more excitation sources 65 are provided. In certain aspects, an excitation source 65 includes a laser, but other sources such as LEDs, arc lamps, white light sources or other sources or devices capable of emitting radiation of a desired wavelength or within a desired wavelength range may be used. A turning mirror 62 is included in certain aspects to provide for scanning of the light source(s) 65 over the sample and/or scanning the field of view of the imaging device 70 over the sample. Imaging device 70 in certain aspects includes a camera or other light detection device such as a CCD, an APD, a photodiode or other device capable of detecting radiation.

Figure 5:
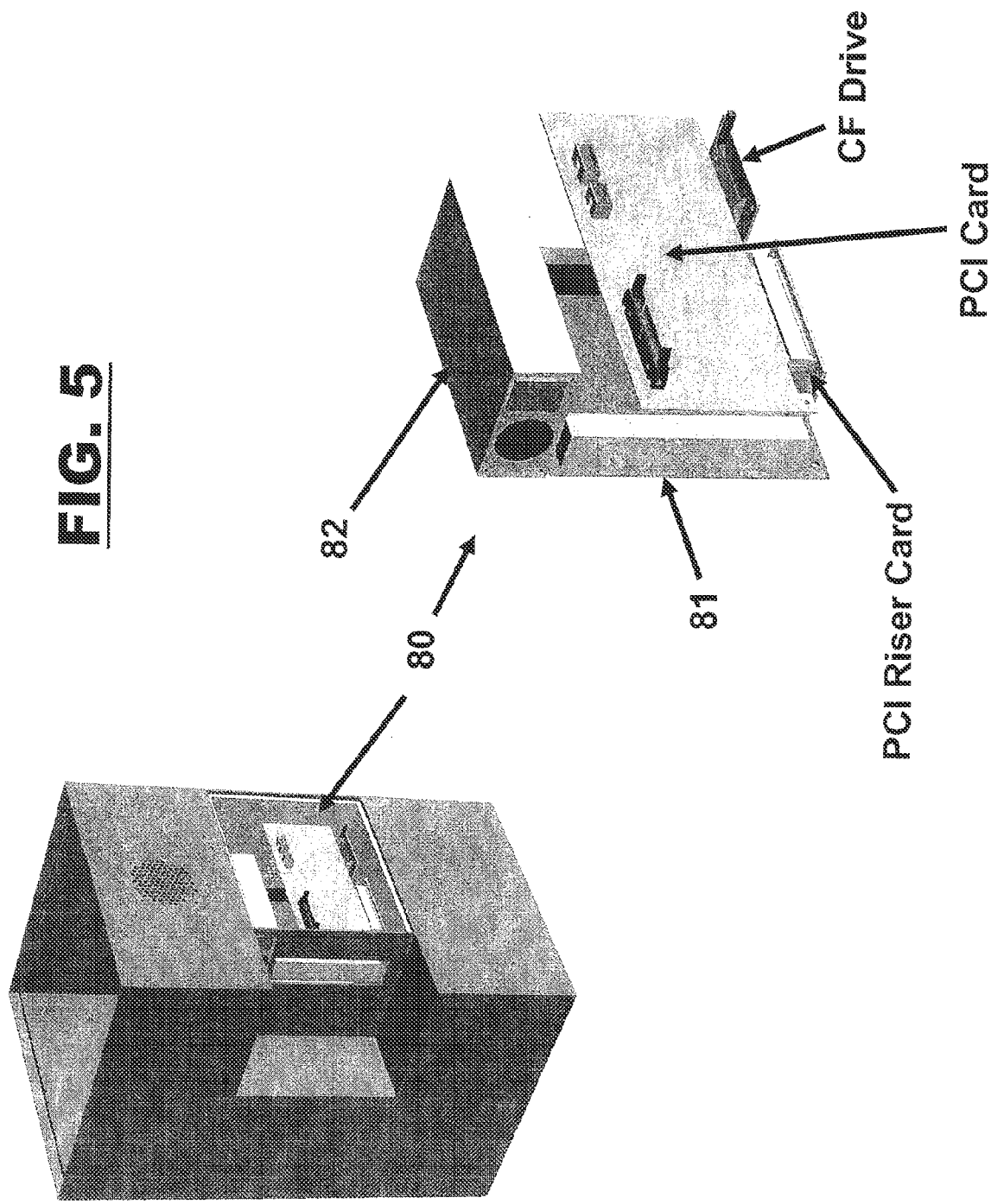
FIG. 5 illustrates a perspective view of the animal imaging system of FIG. 1, including a control module according to one embodiment.

FIG. 5 illustrates components of control system 80 according to one embodiment. In certain aspects, control system 80 includes an intelligence module such as a processor 81 coupled to a mother board. Various input/output (I/O) connectors (not shown) allow for communication with components of system 10. Examples of communication include sending control signals to components of imaging system 60, receiving data (e.g., image data) signals from imaging system 60, receiving data signals from a component on platform 25 of drawer 20, or providing control signals to or receiving data signals from components of a sample holding member mounted to platform 25. For example, platform 25, or a sample holding member docked in platform 25, may include one or more physiological monitors for monitoring physiological characteristics of a live animal sample; these monitors may require control signals from control system 80 and/or they may provide data signals to control system 80. Control system 80 in certain aspects includes one or more external connectors for connecting with external systems. Examples of external connectors might include a PCI card connector, a CF drive, a USB port, a Firewire port, and/or any other connector that enables connection to an external device, network or system. A power source 82 provides power for internal components of system 10 as well as components of control system 80.

Figure 6:
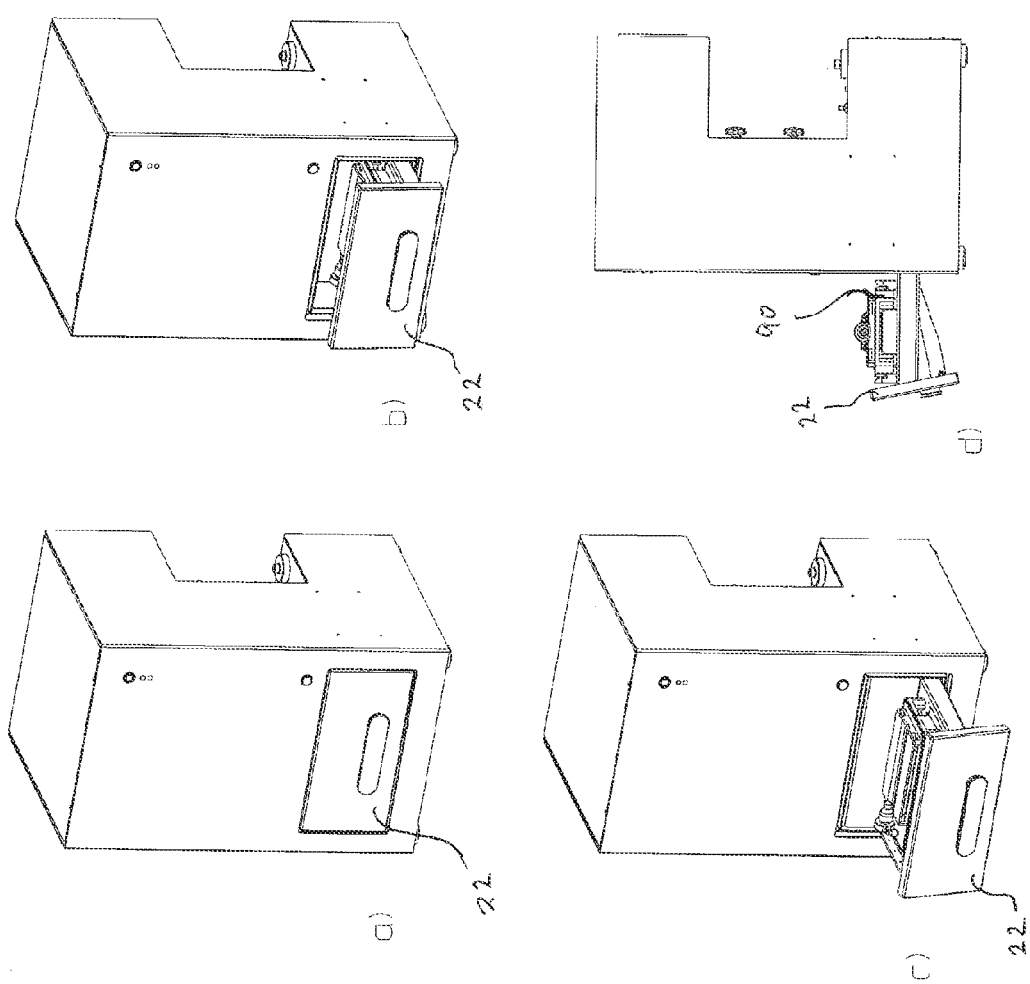
FIG. 6 illustrates various perspective and side views of the animal imaging system of FIG. 1.

According to one embodiment, drawer 20 includes a door or drawer front that is configured to drop out of the way when the drawer is in the extended state to allow for unobstructed access to the platform 25. FIG. 6a shows the sample platform drawer 20 in a closed state; FIG. 6b shows the sample platform drawer 20 opening and extending, and FIG. 6c shows the sample platform drawer in an extended state with the door 22 dropped down. FIG. 6d shows a side view of the sample platform drawer 20 in an extended state with the door 22 dropped down. The unobstructed access to platform 20 provided when the door is dropped down is advantageous to allow a user to easily and conveniently manipulate a sample on platform 25 or to dock a sample holding member 90, such as a removable carrying tray, onto platform 25 and manipulate a sample on the sample holding member 90. For example, manipulating a sample might include attaching or adjusting a nosecone (e.g., for anesthesia delivery) on a live animal sample, applying or adjusting restraints on a live animal sample and applying or adjusting physiological monitors to a live animal sample.

Figure 12:
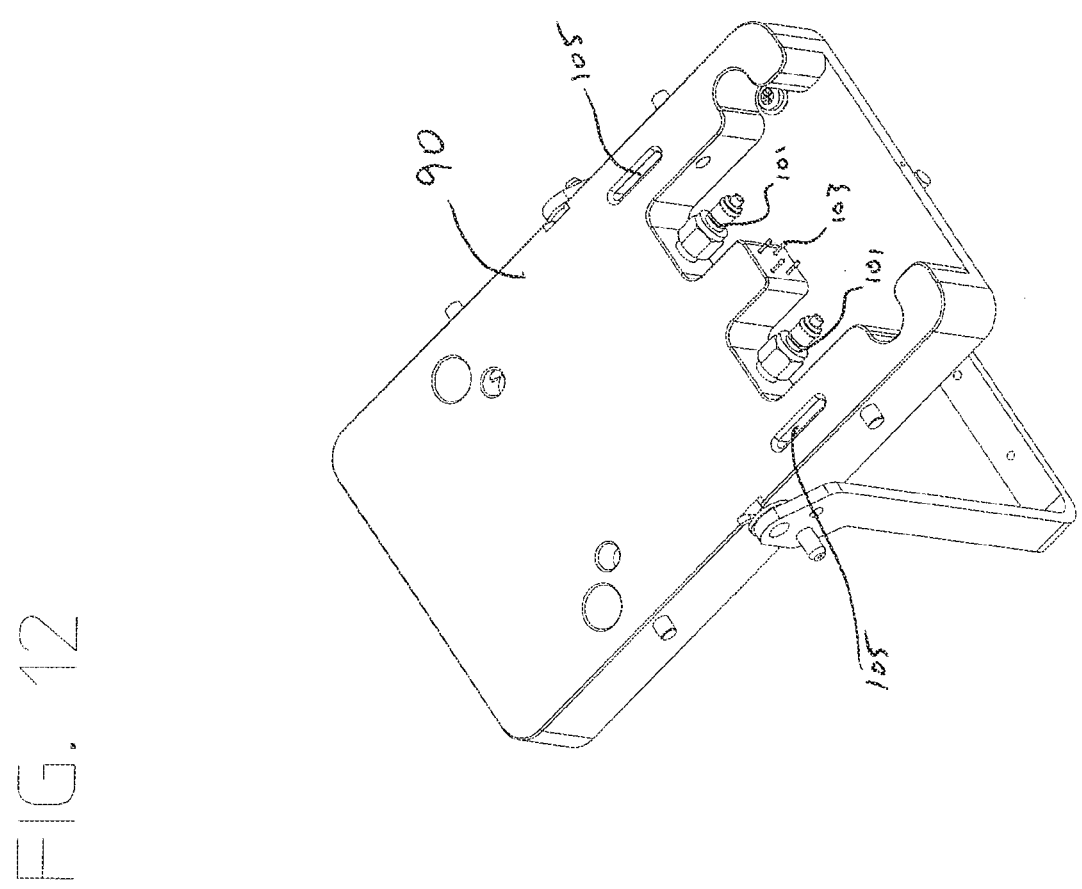
FIG. 12 illustrates a backside of a sample carrying tray including ports and connectors according to one embodiment.

In certain embodiments, a sample carrying tray 90 may be docked (e.g., securely attached to platform 25) and undocked to facilitate carrying of a sample to and from the imaging system 10. FIG. 7 shows un-docking (and also docking) of a sample carrying tray 90 according to one embodiment. In certain aspects, a cam release mechanism is used to dock and undock sample carrying tray 90 from drawer platform 25. A handle 91 is provided to move coupling elements on sample holding tray 90 so as to engage with corresponding coupling elements on platform 90. When tray 90 is placed properly on platform 25 for docking, corresponding coupling elements on platform 25 receive the coupling elements of tray 90. When the handle is activated, e.g., moved from an unlocked state as shown in FIG. 7c toward a locked state as shown in FIG. 7a. (in a locked state the handle detents into a locking position such that the handle is in a folded-down position proximal to the periphery of tray 90 as shown in FIG. 8a), the coupling elements on tray 90 engage the coupling elements of platform 25 to secure tray 90 to platform 25. Removing, or undocking, of the tray 90 from platform 25 is shown in series in FIGS. 7a to 7c: FIG. 7a shows a sample carrying tray 90 with a handle 91 between a locked and an unlocked state; FIG. 7b shows the sample tray 90 with the handle 91 in an unlocked state; FIG. 7c shows the sample tray 90 removed from the sample platform drawer 20. FIGS. 12 and 13, which will be discussed in more detail below, illustrate details of coupling elements of carrying tray 90 and platform 25, respectively, according to one embodiment.

Figure 8:
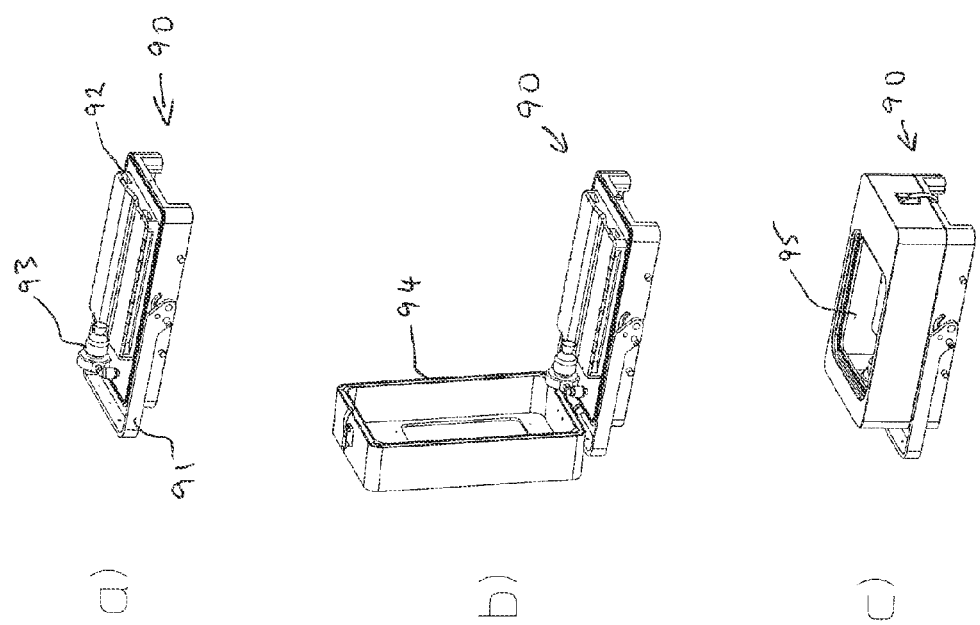
FIG. 8 illustrates perspective views of a sample carrying tray according to one embodiment.

FIG. 8 illustrates a sample holding tray 90 according to one embodiment. Sample holding tray 90, in one embodiment, includes handle 91 and a sample receiving platform 92. For embodiments related to animal imaging, sample carrying tray may also include a nosecone mount 93 for mounting a nosecone thereon. Nosecone mount 93, in certain aspects includes one or more conduits for providing a fluid path between an attached nosecone and a fluid source, e.g., an anesthesia source. A nosecone conduit can also provide a venting path, e.g., for exhausting fluid from the nosecone end. Handle 91 also allows for carrying of the tray. In certain aspects, as described above, handle 91 is part of a mechanism for docking and undocking tray 90 from platform 25, or other docking station. It should be appreciated that a handle is not needed and that a different coupling activation element may be used, or that a handle may be present, yet another coupling activation element also be present.

In certain aspects, as shown in FIG. 8b, an optional lid is included to cover tray 90 and provide a controlled environment within the volume defined by the lid. In certain aspects, lid 94 includes a window 95 that allows viewing or imaging a sample located on platform 92 of tray 90. FIG. 8c shows a tray 90 with a closed lid 94. When docked on drawer platform 25 of system 10, the window 95 allows for imaging of the sample by imaging system 60. In certain aspects, window 95 is transparent to a desired range of radiation wavelengths. For example, for fluorescent imaging embodiments, window 95 is transparent to excitation and fluorescent wavelengths of interest. Lid 94 is particularly useful to environmentally isolate a sample on the tray platform. For example, in the case of immune compromised mice (SCID mice) or other animals, a controlled environment provided by the lid eliminates or reduces issues of exposure when transporting the animal to and from the imaging system from a controlled environment such as a laminar flow hood station. In certain aspects, tray 90 includes one or more gas sources such that when the lid is closed, a pressurized volume of oxygen and/or anesthesia, for example, can be supplied to provide a controlled environment when transporting the sample. In other aspects, the volume would load (e.g., pressurize) when docked, and during transport, a metered dispense of gas (e.g., anesthesia) could be provided. An indicator, such as a visual indicator or audible indicator, is provided in certain aspects, to inform the user as to how much time may be remaining before re-docking in a sterile environment may be required. In certain aspects, the tray (with a lid) fills and pressurizes the onboard gas source when docked in the imaging system or a remote sterile preparation station. The gas is metered when the tray is not mounted, providing gas (e.g., oxygen and/or anesthesia) to an animal sample during transport.

Figure 9:
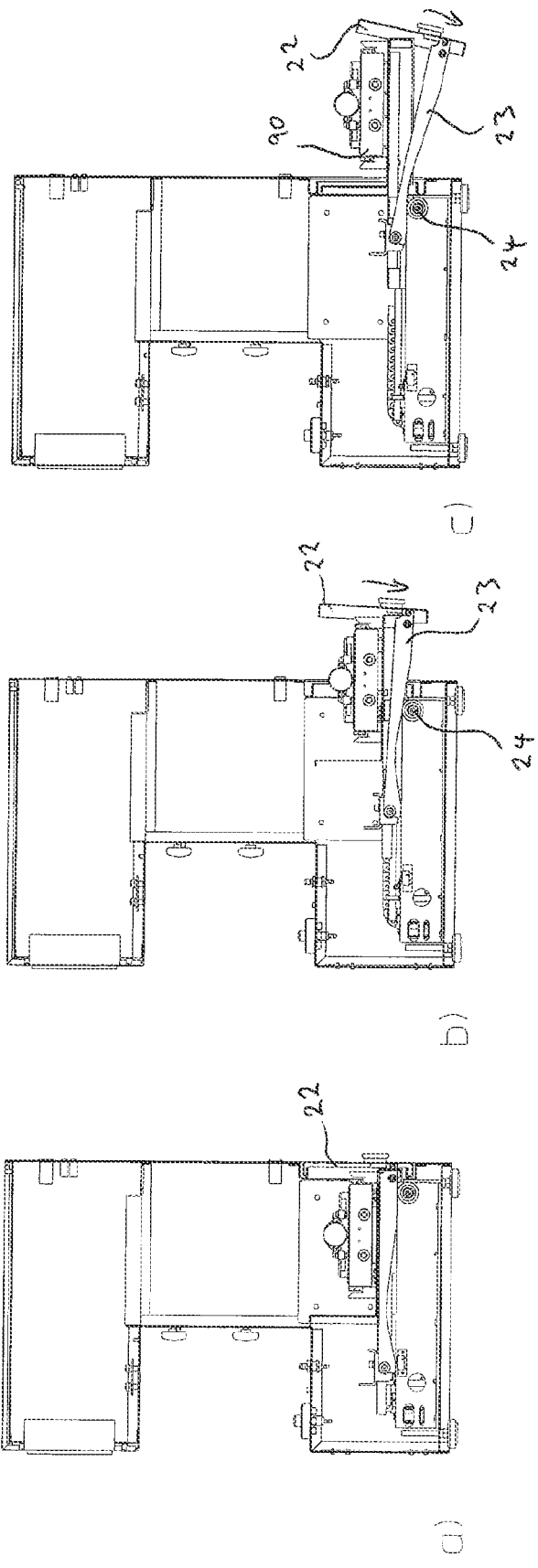
FIG. 9 illustrates side views of the animal imaging system including a sample platform drawer coupled with a door via a cam mechanism configured to lower the door as the drawer extends outward from the housing.

According to one embodiment, imaging system 10 includes a mechanism to lower a door or drawer cover out of the way to provide unhindered access to a drawer platform 25. FIG. 9 illustrates side views of an animal imaging system 10 including a sample platform drawer 20 coupled with a door 22 via a cam mechanism configured to lower the door as the drawer extends outward from the housing: FIG. 9a shows the door in a closed state; FIG. 9b shows the door lowering as the drawer extends; FIG. 9c shows the door in a lowered state when the drawer is in an extended state. As shown, the cam mechanism includes a cam bar 23 that couples the door 22 with platform 25. A roller or other bearing 24 attached to the fixed bearing assembly (See FIG. 3) engages an underside of bar 23. As the drawer 20 is extended outward, the curved portion of bar 22 travels over the roller and lowers the door 22 (It should be appreciated that the bar need not have a curved portion). In this manner, the door is lowered to a position that allows for easier access to platform 25. As the drawer retracts into the housing structure, door 22 is raised by the cam mechanism to a position to engage the housing structure and provide a seal. It should be appreciated that other mechanisms may be used to lower or otherwise reposition door 22 so as to facilitate access to platform 25. For example, the door may be unattached to drawer 20, such that the door may simply be removed, or the door may be configured to slide or retract into a portion of housing structure (e.g., downwards, upwards, sideways, etc.) separate from, or as part of, the operation of drawer 20.

According to one embodiment, when door 22 is closed, the seal between door 22 and the housing structure provides a substantially light-tight fit yet also provides an air path to facilitate venting of an interior of the housing structure of system 10. FIG. 10 shows a door having a light-tight venting seal according to one embodiment. FIG. 10*a* illustrates a side view of a door 22 in a closed state, including a light-blocking vent seal according to one embodiment, and FIG. 10*b* shows a close-up of the light-blocking vent seal of FIG. 10*a*. In certain aspects, the light-blocking vent seal keeps a sufficient amount of light out of the interior so as to not interfere with imaging, and the seal also provides an air path to allow for venting of the interior. The seal, in certain aspects, does not eliminate all light, such that imaging application requiring several minutes or even hours of acquisition time may detect interfering light from the exterior, however, the seal eliminates a majority of the light sufficient to not influence imaging applications needing up to seconds to a minute or so of image acquisition time. In general, the seal attenuates infiltrating light and acts as a light labyrinth providing a reflective path, with multiple surfaces, that allows for radiation to be reflected and absorbed at each surface, and with no direct path for radiation entry and exit. The seal also provides protection to users from laser radiation internal to the housing structure as no single reflection can direct radiation from an internal laser source to the exterior.

Figure 11:
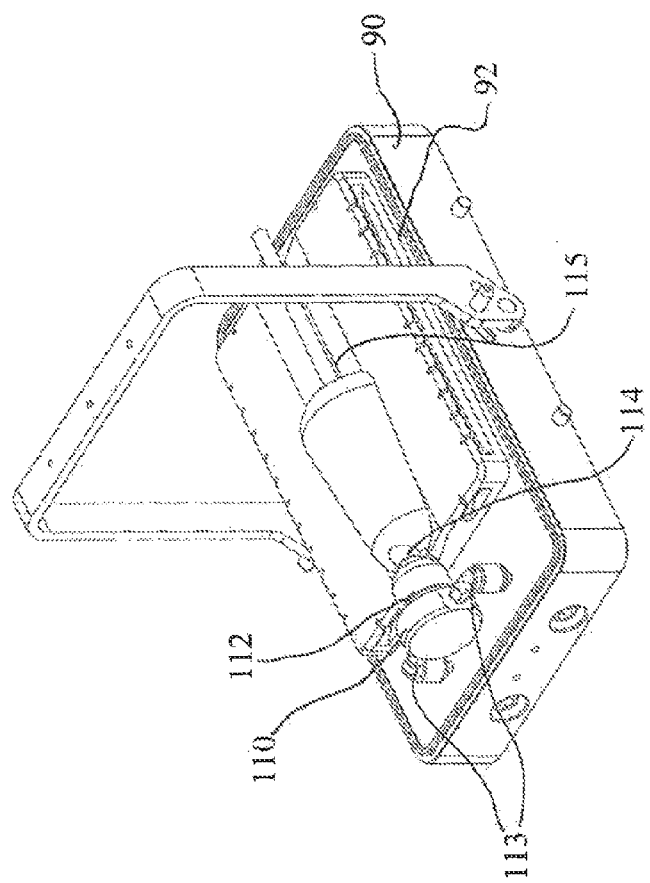
FIG. 11 illustrates a sample carrying tray including a nosecone mount according to one embodiment.

FIG. 11 shows a carrying tray 90 including a nosecone mount 110 with an attached nosecone 114 according to one embodiment. Nosecone mount 110 includes a ball joint 112 coupled with a pair of elbow fittings 113. The ball joint 112 provides rotational movement about an axis of the ball joint, and the elbow fittings allow for a height adjustment of the nosecone 114, e.g., by rotating the ball joint 112 about an axis defined by the pair of elbow fittings 113. As shown, the axis defined by the elbow fittings is parallel to the plane of the platform 92 and perpendicular to the ball joint axis. It should be appreciated that these two axes need not be perpendicular, and the elbow fitting axis need not be parallel to the platform surface. The extra degrees of freedom provided by nosecone mount 110 allow a user to more effectively manipulate a nosecone fitting on a live animal. For example, the user may rotate the animal and the ball joint simultaneously rather than have to remove the nosecone from the animal, rotate the animal and then replace the nosecone. In certain aspects, the ball joint 112 includes one or more conduits to allow for fluid (e.g., gas such as anesthesia) to be provided to the end of an attached nosecone 114 and/or to evacuate fluid from the end of the nosecone 114. As shown, carrying tray platform 92 in certain aspects includes a v-groove 115 or other feature to facilitate alignment and holding of a live animal on platform 92. Proper positioning of the sample can be beneficial for accurate imaging. Restraints are provided in certain aspects to hold the animal securely to the platform. In one aspect, magnetic restraints are provided. For example, the platform or at least a portion of the platform may comprise a ferrous material. A restraint may include a band with magnetic end (e.g., attached to a magnet) that magnetically couples with the platform to restrain the sample thereto.

FIGS. 12 and 13 show coupling mechanism components on the underside of a carrying tray 90 and on a platform 25 of drawer 20, respectively, according to one embodiment. As shown, a pair of gas ports 101 on tray 90 are positioned to engage with corresponding connectors 102 on platform 25 of a drawer 20. Similarly, an electrical connector 103 on tray 90 is positioned to engage with corresponding connectors 104 on platform 25. Also, alignment grooves 105 mate with pin 106 on platform 25 to provide for registration (e.g., correct positioning) for docking of tray 90 on platform 25. When properly positioned on pins 106, and the cam mechanism activated by engaging handle 91, tray 90 slides to securably engage and dock with platform 25. As the tray slides, the connectors (e.g., connectors 101 and 103) engage corresponding connectors (e.g., 102 and 104). It should be appreciated that additional or alternate connectors might be included on tray 90 and platform 25 for operating or communicating with various devices adapted for monitoring characteristics of the sample or for controlling various characteristics of the tray 90 such as temperature control module for controlling the temperature of the tray platform. For example, where the sample is a live animal such as a mouse, the additional connectors might include connectors for monitoring the physiological condition of the animal. Examples might include connections to monitors on the carrying tray platform 92, such as respiration monitors, heart rate monitors, blood pressure monitors and temperature probes and monitors (e.g., for monitoring and/or regulating interior and/or external sample temperatures). Various monitors can be placed at desired locations on the carrying tray platform 92.

According to one embodiment, tray 90 can be docked on platform 25 of drawer 20 in imaging system 10, and then removed and transported to another docking station at another location. One example is a preparation station in a laboratory setting. the preparation station or other location, in certain aspects is equipped with a docking station including the docking features as described above with reference to platform 25 of the drawer. In this manner, user interaction with the imaging system is enhanced. For example, one or multiple docking stations could be used for preparation of samples or concurrent preparation of samples on different trays (docked or undocked), and SCID imaging can be facilitated by using a laminar flow hood station nearby with a docking station so that the sample may be prepared nearby. The docking tray and docking stations also provide for ease of use and repeatability of docking.

In certain aspects, a sample carrying tray can mount in an imaging system housing, and another location can provide another complementary mounting or docking station with gas and/or electrical and or other connections that allow for sample mounting, positioning and other preparation activities, including for example, dye labeling injections, shaving, etc. Different preparation locations may be equipped with docking stations that provide different functionality and connections to a docked tray.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A carrying tray for holding and transporting a living animal, the tray comprising:
   a platform that presents a surface for receiving and supporting a live animal;
   a nosecone mounted to the platform, the nosecone adapted to receive the nose of a live animal supported on the platform;

one or more gas ports on an underside of the platform for coupling with an external source of gas and/or fir exhausting gas;
one or more electrical connectors on an underside of the platform for coupling with external power and/or signal sources; and
a connection mechanism adapted to removably engage with a tray receiving member of an animal imaging system or a sterile workstation such that when the tray engages the tray receiving member, the one or more gas ports and the one or more electrical connectors automatically mate with corresponding elements on the tray receiving member,
wherein the connection mechanism includes a handle coupled to a first portion of a locking mechanism, wherein the tray receiving member includes a second portion of the locking mechanism, wherein the first portion of the locking mechanism engages the second portion when the handle is moved from a release position to a locking position, and wherein the first and second portions disengage when the handle is moved from the locking position to the release position.

2. The tray of claim 1, wherein the platform includes one or more valves associated with the one or more gas ports, wherein each valve is automatically actuated when the tray engages the tray receiving member.

3. The tray of claim 1, further including one or more restraints for holding the live animal on the surface.

4. The tray of claim 1, wherein a portion of the surface comprises a magnetic material or one or more embedded magnets, the tray further including a magnetic restraint for holding the live animal on the surface, said magnetic restraint including a magnet that magnetically couples with the magnetic material.

5. The tray of claim 1, further including an air-tight lid that provides an enclosed volume when attached to the tray.

6. The tray of claim 5, wherein the lid includes a window that allows radiation of a desired wavelength range to pass.

7. The tray of claim 1, further including a metering system coupled to the external. gas source, the metering system configured to automatically provide metered doses of gas into the nosecone.

8. A carrying tray of claim 1 in combination with a docking station comprising said tray receiving member, said tray receiving member having one or more corresponding port connectors for mating with the one or more gas ports of the tray, and one or more electric coupling members for mating with the one or more electrical connectors of the tray.

9. The tray and docking station of claim 8, wherein said docking station is located in one of a sterile workstation or an animal imaging system.

10. A carrying tray for holding and transporting a living animal, the tray comprising:
a platform that presents a surface for receving and supporting a live anumal;
a nosecone mounted to the platform, the nosecone adapted to receive the nose of a live animal supported on the platform;
one or more gas ports on an underside o1 the platform for coupling with an external source of gas and/or for exhausting gas;
one or more electrical connectors on an underside of the platform for coupling with external power and/ or signal sources;
a connection mechanism adapted to removably engage with a tray receiving member of an animal imaging system or a sterile workstation such that when tray engages the tray receiving member, the one or more gas ports and the one or more electrical connectors automatically mate with corresponding elements on the tray receiving member; and
a nosecone mount for mounting the nosecone to the platform, the mount comprising:
a ball joint having a conduit for providing fluid to the nosecone to or from a remote location, wherein the ball joint enables rotational movement of the nosecone about a ball joint axis; and
a pair of elbow fittings coupled to the ball joint and configured to couple with the platform, the elbow fittings enabling rotation of the ball joint about an axis defined by the elbow fittings.

11. The tray of claim 10, wherein the ball joint axis is substantially perpendicular to the axis defined by the elbow fittings.

12. The tray of claim 10, wherein the remote location includes one of a gas source, a filter and a reservoir.

13. A carrying tray for holding and transporting a living animal, the tray comprising:
a platform that presents a surface for receiving and supporting a live animal;
a nosecone mounted to the platform, the nosecone adapted to receive the nose of a live animal supported on the platform;
one or more gas ports on an underside of the platform for coupling with an external source of gas and/or for exhausting gas;
one or more electrical connectors on an underside of the platform for coupling with external power and/or signal sources;
a connection mechanism adapted to removably engage with a tray receiving member of an animal imaging system or a sterile workstation such that when engaged the one or more gas ports and the one or more electrical connectors mate with corresponding elements on the tray receiving member; and
a nosecone mount for mounting the nosecone to the platform, the mount comprising:
a ball joint having a conduit for providing fluid to the nosecone to or from a remote location, wherein the ball joint enables rotational movement of the nosecone about a ball joint axis; and
a pair of elbow fittings coupled to the ball joint and configured to couple with the platform, the elbow fittings enabling rotation of the ball joint about an axis defined by the elbow fittings.

14. The tray of claim 13, wherein the ball joint axis is substantially perpendicular to the axis defined by the elbow fittings.

15. The tray of claim 13, wherein the remote location includes one of a gas source, a filter and a reservoir.

* * * * *